(12) United States Patent
Rotem et al.

(10) Patent No.: US 8,308,457 B2
(45) Date of Patent: Nov. 13, 2012

(54) PERISTALTIC INFUSION PUMP WITH LOCKING MECHANISM

(75) Inventors: Shachar Rotem, M.P. Hefer (IL); Ori Goldor, Amikam (IL)

(73) Assignee: Q-Core Medical Ltd., Petach Tikva (IL)

( * ) Notice: Subject to any disclaimer, the term of this patent is extended or adjusted under 35 U.S.C. 154(b) by 593 days.

(21) Appl. No.: 12/464,202

(22) Filed: May 12, 2009

(65) Prior Publication Data

US 2009/0221964 A1 Sep. 3, 2009

Related U.S. Application Data

(63) Continuation-in-part of application No. 11/791,599, filed as application No. PCT/IL2005/001249 on Nov. 24, 2005, now Pat. No. 8,029,253, application No. 12/464,202, which is a continuation-in-part of application No. PCT/IL2007/001399, filed on Nov. 13, 2007.

(30) Foreign Application Priority Data

Nov. 24, 2004 (IL) .......................................... 165365
Nov. 13, 2006 (IL) .......................................... 179228

(51) Int. Cl.
*F04B 45/06* (2006.01)
(52) U.S. Cl. ............................ 417/479; 604/153; 417/53
(58) Field of Classification Search .................. 417/474, 417/478, 479, 53; 604/151, 153
See application file for complete search history.

(56) References Cited

U.S. PATENT DOCUMENTS

| | | |
|---|---|---|
| 2,056,322 A | 10/1936 | Hoppe |
| 2,743,898 A | 5/1956 | King |
| 3,443,585 A | 5/1969 | Reinicke |
| 3,982,722 A | 9/1976 | Bernard |
| 3,982,725 A | 9/1976 | Clark |
| 4,014,318 A | 3/1977 | Dockum et al. |
| 4,039,269 A | 8/1977 | Pickering |
| 4,155,362 A | 5/1979 | Jess |
| 4,236,880 A | 12/1980 | Archibald et al. |
| 4,270,532 A | 6/1981 | Franetzki et al. |

(Continued)

FOREIGN PATENT DOCUMENTS

DE 10118086 A 7/2002

(Continued)

OTHER PUBLICATIONS

Chinese Patent Application No. 200780041966.8 Official Action dated Jul. 13, 2010.

(Continued)

*Primary Examiner* — Charles Freay
*Assistant Examiner* — Patrick Hamo
(74) *Attorney, Agent, or Firm* — Vladimir Sherman; Professional Patent Solutions

(57) ABSTRACT

A medical device includes an interface unit body, which is configured to hold a portion of a flexible infusion tube. A hinge insert is fixed to the interface unit body and is configured to engage a hinge receptacle, which defines a hinge axis, on an infusion pump. A catch insert is fixed to the interface unit body and is configured to lock onto a catch receptacle on the infusion pump upon rotation of the mechanical interface unit about the hinge axis while the hinge insert engages the hinge receptacle, so as to bring the tube into engagement with a peristaltic mechanism of the infusion pump in order to enable the peristaltic mechanism to propel a fluid through the tube.

20 Claims, 6 Drawing Sheets

U.S. PATENT DOCUMENTS

| | | | |
|---|---|---|---|
| 4,320,781 A | 3/1982 | Bouvet et al. | |
| 4,450,375 A | 5/1984 | Siegal | |
| 4,489,863 A | 12/1984 | Horchos et al. | |
| 4,682,135 A | 7/1987 | Yamakawa | |
| 4,728,265 A | 3/1988 | Cannon | |
| 4,741,736 A | 5/1988 | Brown | |
| 4,893,991 A | 1/1990 | Heminway et al. | |
| 4,978,335 A | 12/1990 | Arthur, III | |
| 5,096,385 A | 3/1992 | Georgi et al. | |
| 5,103,211 A | 4/1992 | Daoud et al. | |
| 5,152,680 A | 10/1992 | Okada | |
| 5,165,874 A | 11/1992 | Sancoff et al. | |
| 5,213,483 A | 5/1993 | Flaherty et al. | |
| 5,222,946 A | 6/1993 | Kamen | |
| 5,257,978 A | 11/1993 | Haber et al. | |
| 5,290,158 A | 3/1994 | Okada | |
| 5,395,320 A | 3/1995 | Padda et al. | |
| 5,429,485 A | 7/1995 | Dodge | |
| 5,499,969 A | 3/1996 | Beuchat et al. | |
| 5,509,439 A | 4/1996 | Tantardini | |
| 5,527,295 A | 6/1996 | Wing | |
| 5,575,309 A | 11/1996 | Connell | |
| 5,577,891 A | 11/1996 | Loughnane et al. | |
| 5,593,134 A | 1/1997 | Steber et al. | |
| 5,658,252 A | 8/1997 | Johnson | |
| 5,683,233 A | 11/1997 | Moubayed et al. | |
| 5,782,805 A | 7/1998 | Meinzer et al. | |
| 5,807,322 A | 9/1998 | Lindsey et al. | |
| 5,896,076 A | 4/1999 | Van Namen | |
| 5,996,964 A | 12/1999 | Ben-Shalom | |
| 6,095,189 A | 8/2000 | Ben-Shalom | |
| 6,164,921 A | 12/2000 | Moubayed et al. | |
| 6,165,874 A * | 12/2000 | Powell et al. | 438/478 |
| 6,203,296 B1 | 3/2001 | Ray et al. | |
| 6,261,262 B1 | 7/2001 | Briggs et al. | |
| 6,339,410 B1 | 1/2002 | Milner et al. | |
| 6,371,732 B1 | 4/2002 | Moubayed et al. | |
| 6,450,773 B1 | 9/2002 | Lipton | |
| 6,537,244 B2 | 3/2003 | Paukovits et al. | |
| 6,692,241 B2 | 2/2004 | Watanabe et al. | |
| 6,733,476 B2 | 5/2004 | Christenson et al. | |
| 7,018,361 B2 | 3/2006 | Gillespie, Jr. et al. | |
| 7,022,075 B2 | 4/2006 | Grunwald et al. | |
| 7,122,026 B2 | 10/2006 | Rogers et al. | |
| 7,163,385 B2 | 1/2007 | Gharib et al. | |
| 2002/0156402 A1 | 10/2002 | Woog et al. | |
| 2002/0165503 A1 | 11/2002 | Morris et al. | |
| 2003/0040700 A1 | 2/2003 | Hickle et al. | |
| 2003/0182586 A1 | 9/2003 | Numano | |
| 2004/0181314 A1 | 9/2004 | Zaleski | |
| 2004/0191112 A1 | 9/2004 | Hill et al. | |
| 2005/0088409 A1 | 4/2005 | Van Berkel | |
| 2006/0051218 A1 | 3/2006 | Harttig | |
| 2007/0269324 A1 | 11/2007 | Goldor et al. | |
| 2008/0095649 A1 | 4/2008 | Ben-Shalom et al. | |

FOREIGN PATENT DOCUMENTS

| | | |
|---|---|---|
| EP | 0215249 A1 | 3/1987 |
| EP | 0225158 A2 | 6/1987 |
| FR | 2632529 A | 12/1989 |
| JP | 60043188 A | 3/1985 |
| JP | 6-169992 A | 6/1994 |
| JP | 2002-57738 A | 2/2002 |
| JP | 2004141418 A | 5/2004 |
| WO | 9116933 A1 | 11/1991 |
| WO | 03027503 A1 | 4/2003 |
| WO | 2008059492 A2 | 5/2008 |
| WO | 2008059493 A2 | 5/2008 |
| WO | 2008059494 A2 | 5/2008 |
| WO | 2008059495 A2 | 5/2008 |
| WO | 2008059496 A2 | 5/2008 |
| WO | 2008059498 A2 | 5/2008 |
| WO | 2008059499 A2 | 5/2008 |
| WO | 2008130644 A1 | 10/2008 |

OTHER PUBLICATIONS

U.S. Appl. No. 11/791,599 Official dated Aug. 19, 2010.
U.S. Appl. No. 12/514,311 Official dated Sep. 16, 2010.
Honeywell Sensing and Control, "FSS1500NSB force sensor", Golden Valley, Minnesota, USA, 1998-2004 http://sccatalog.honeywell.com/imc/printfriendly.asp?FAM=force&PN=FSS1500NSB.
U.S. Appl. No. 12/644,027 Official Action dated Apr. 28, 2011.
U.S. Appl. No. 11/791,599 Official Action dated Mar. 31, 2011.
European Patent Application # 10192477.7 Search Report dated May 10, 2011.
U.S. Appl. No. 10/535,103 Official Action dated Feb. 2, 2009.
International Application PCT/IL2007/001398 Search Report dated Jun. 11, 2008.
International Application PCT/IL2007/001398 Patentability Report dated May 28, 2009.
International Application PCT/IL2007/001399 Search Report dated Jun. 4, 2008.
International Application PCT/IL2007/001399 Patentability Report dated May 19, 2009.
International Application PCT/IL2007/001400 Search Report dated Jul. 15, 2008.
International Application PCT/IL2007/001400 Patentability Report dated May 28, 2009.
International Application PCT/IL2007/001401 Search Report dated Sep. 24, 2008.
International Application PCT/IL2007/001401 Patentability Report dated May 28, 2009.
International Application PCT/IL2007/001402 Search Report dated Jun. 20, 2008.
International Application PCT/IL2007/001402 Patentability Report dated May 28, 2009.
International Application PCT/IL2007/001404 Search Report dated Jul. 14, 2008.
International Application PCT/IL2007/001404 Patentability Report dated May 28, 2009.
International Application PCT/IL2007/001405 Search Report dated Jul. 21, 2008.
International Application PCT/IL2007/001405 Patentability Report dated May 28, 2009.
International Application PCT/IL2005/001249 Search Report dated Apr. 5, 2006.
Rotem et al., U.S. Appl. No. 12/463,399 "Magnetically Balanced Finger-Type Peristaltic Pump" filed on May 10, 2009.
Chinese Patent Application No. 200580045471.3 "Finger-type peristaltic pump" Official Action dated Jul. 18, 2008.
U.S. Appl. No. 09/125,438 Official dated Jul. 15, 1999.
U.S. Appl. No. 09/125,438 Official dated May 3, 1999.
European Application No. 05810500.8 Official Action dated Jul. 6, 2009.
International Application PCT/IL1997/000289 Search report dated Jan. 27, 1998.
International Application PCT/IL1997/000290 Search Report dated Jan. 27, 1998.
International Application PCT/IL2003/000947 Search Report dated Mar. 3, 2004.
U.S. Appl. No. 12/463,399 Official Action dated Jul. 21, 2011.
U.S. Appl. No. 12/514,310 Official Action dated Jul. 21, 2011.

* cited by examiner

PERISTALTIC INFUSION PUMP WITH LOCKING MECHANISM

CROSS-REFERENCE TO RELATED APPLICATIONS

This application is a continuation-in-part of U.S. patent application Ser. No. 11/791,599, filed May 24, 2007, in the national phase of PCT/IL2005/001249, filed Nov. 24, 2005, and of PCT Patent Application PCT/IL2007/001399, filed Nov. 13, 2007. The disclosures of all of these related applications are incorporated herein by reference.

FIELD OF THE INVENTION

The present invention relates generally to medical devices, and specifically to infusion pumps.

BACKGROUND OF THE INVENTION

Various types of medical infusion pumps are known in the art. One common type of infusion pump is a peristaltic pump, in which fluid is made to flow through an elastic tube by external compression of the tube. Typically, a peristaltic mechanism, such as a set of cams or fingers, compresses the tube in a cyclic pattern at a sequence of locations along the length of the tube, so as to cause the fluid to flow through the tube at a desired volumetric rate. Peristaltic infusion pumps are described, for example, in U.S. Pat. Nos. 5,290,158, 5,395,320, and 5,807,322, whose disclosures are incorporated herein by reference, as well as in the above-mentioned PCT patent applications.

SUMMARY OF THE INVENTION

One advantage of peristaltic pumps in medical applications is that the pump mechanism is external to the flexible tube containing the fluid, thus preserving the sterility of the fluid flowing through the tube. The tube is typically part of a disposable infusion kit, while the pump itself (which may include the complete pumping mechanism, as well as a pressure sensor module) is reused many times. Embodiments of the present invention that are described hereinbelow provide devices and methods that simplify the task of attaching the infusion tube to the pump prior to use, while ensuring a secure, reliable mechanical connection between the pump mechanism and the tube.

There is therefore provided, in accordance with an embodiment of the present invention, a medical apparatus, including an infusion pump, which includes a pump body and a peristaltic mechanism, which protrudes from the pump body and is configured to exert a force on a flexible infusion tube so as to propel a fluid through the tube. A hinge receptacle is fixed to the pump body and defines a hinge axis, and a catch receptacle is also fixed to the pump body. A mechanical interface unit is configured to hold a portion of the tube, and includes a hinge insert, which is configured to engage the hinge receptacle. A catch insert is configured to lock onto the catch receptacle upon rotation of the mechanical interface unit about the hinge axis while the hinge insert engages the hinge receptacle, so as to bring the tube into engagement with the peristaltic mechanism.

In a disclosed embodiment, the peristaltic mechanism includes multiple fingers, which are driven to compress and release the tube in a predetermined cyclic pattern.

In some embodiments, the peristaltic mechanism has a linear configuration, and the mechanical interface has an elongated shape corresponding to the linear configuration of the peristaltic mechanism.

In one embodiment, the hinge receptacle includes an axle, and the hinge insert includes a saddle, which fits over the axle. The axle and saddle may be split so as to define a channel for receiving the portion of the tube. Additionally or alternatively, the catch insert includes a tooth, and the catch receptacle includes an elastic catch.

In some embodiments, the pump body includes a rim surrounding the peristaltic mechanism, and the mechanical interface unit includes collars, which are fixed to opposing ends of the portion of the tube and lodge against the rim. The infusion pump may include a door, which closes over the rim so as to enclose the peristaltic mechanism. The rim may have openings shaped to receive the tube so that the tube extends through the openings when the door is closed. Typically, the collars are configured to lodge inside the rim and have respective diameters that are larger than the openings so as to prevent axial motion of the tube after the door has been closed.

In a disclosed embodiment, the mechanical interface unit includes an anti-free-flow mechanism, which is configured to prevent flow of the fluid through the portion of the tube until the tube has been brought into engagement with the peristaltic mechanism. Typically, the anti-free-flow mechanism can be opened manually prior to the engagement of the tube with the peristaltic mechanism, and the infusion pump includes a key, which is fixed to the pump body and is configured to release the anti-free-flow mechanism so as to prevent the flow of the fluid through the portion of the tube when the mechanical interface unit is disengaged from the pump. The anti-free-flow may have a non-obstructing position in which the anti-free-flow device does not prevent flow in the conduit, and an obstructing position in which the anti-free-flow device prevents flow in the conduit. The antifree-flow device may be spring biased in the obstructing position, so that when the housing is swung away or detached from the body of the pump, the anti-free-flow device spontaneously may assume its obstructing position. This may prevent unintentional flow in the conduit when the housing is swung out or detached from the body of the pump. The anti-free-flow device may preferably include an override mechanism that allows the anti-free-flow device to be temporarily latched in its non-obstructing position when the housing is swung away or detached from the body in order to allow a segment of conduit to be introduced into the housing. As the housing is brought to a position in which it is attached to the pump, the anti-free-flow device may be brought to its unlatched non-obstructing position, regardless of whether it was previously in its obstructing position or its latched non-obstructing position. The anti-free flow device may prevent flow in the conduit in both directions or only in one direction.

There is also provided, in accordance with an embodiment of the present invention, a medical device, including an interface unit body, which is configured to hold a portion of a flexible infusion tube. A hinge insert is fixed to the interface unit body and is configured to engage a hinge receptacle, which defines a hinge axis, on an infusion pump. A catch insert is fixed to the interface unit body and is configured to lock onto a catch receptacle on the infusion pump upon rotation of the mechanical interface unit about the hinge axis while the hinge insert engages the hinge receptacle, so as to bring the tube into engagement with a peristaltic mechanism of the infusion pump in order to enable the peristaltic mechanism to propel a fluid through the tube.

In a disclosed embodiment, the device includes collars, which are fixed to opposing ends of the portion of the tube and are configured to lodge against a rim surrounding the peristaltic mechanism on the infusion pump. The collars may include connectors, which connect the portion of the flexible infusion tube in the housing to upstream and downstream tube segments.

There is additionally provided, in accordance with an embodiment of the present invention, a method for infusion, including providing a mechanical interface unit, which holds a portion of a flexible infusion tube and includes a hinge insert and a catch insert. The hinge insert in inserted into a hinge receptacle, which defines a hinge axis, on an infusion pump. The mechanical interface unit is rotated about the hinge axis while the hinge insert engages the hinge receptacle, so as to bring the tube into engagement with a peristaltic mechanism of the infusion pump. The infusion pump is actuated while the tube is in engagement with the peristaltic mechanism so as to propel a fluid through the tube.

The present invention will be more fully understood from the following detailed description of the embodiments thereof, taken together with the drawings in which:

DETAILED DESCRIPTION OF EMBODIMENTS

Figure 1:
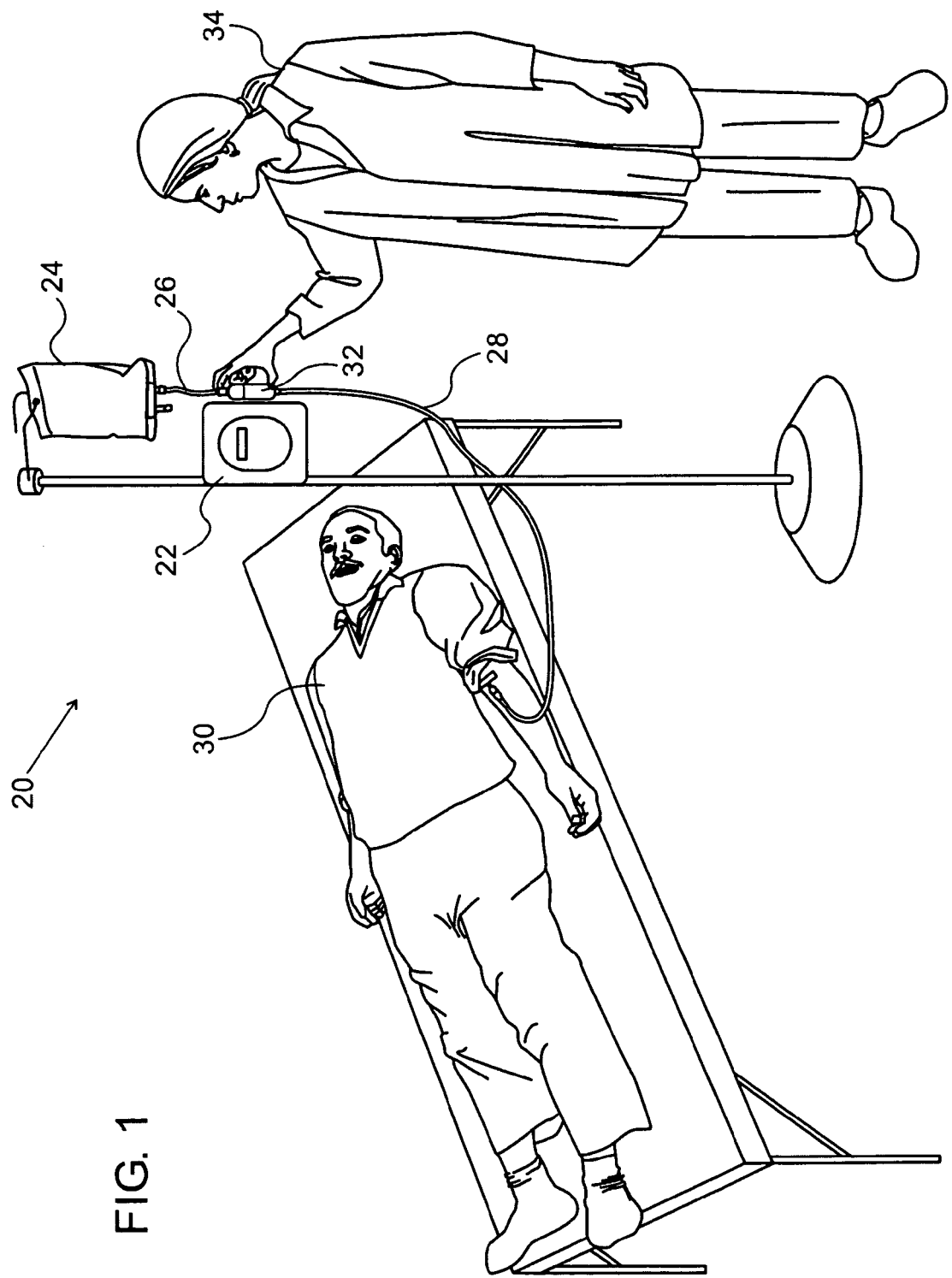
FIG. 1 is a schematic, pictorial illustration of a medical infusion system, in accordance with an embodiment of the present invention.

FIG. 1 is a schematic, pictorial illustration of a medical infusion system 20, in accordance with an embodiment of the present invention. System 20 comprises a peristaltic infusion pump 22, which pumps an infusion fluid from a reservoir 24, through an upstream tube segment 26 (commonly referred to as the "supply line") and a downstream tube segment 28 (commonly referred to as the "patient line"), into a vein of a patient 30. This particular type of infusion system is shown here by way of illustration, but the principles of the present invention, as described hereinbelow, may likewise be applied to other types of peristaltic pumps and in substantially any sort of application that uses such pumps, such as delivery of drugs and of both enteral and parenteral nutrition. Although the pictured embodiment represents a clinical environment, the devices and methods described herein are also suitable for ambulatory and home use, particularly since they can operate even when the pump and reservoir are at the same level as or lower than the patient.

Tube segments 26 and 28 are connected to a mechanical interface unit 32, which couples to pump 32 in a manner that is shown and explained below in greater detail. Unit 32 contains a tube portion (not shown in FIG. 1) that is connected in series with tube segments 26 and 28, thus defining a flow path from reservoir 24 to patient 30. In a typical implementation, tube segments 26 and 28 comprise polyvinyl chloride (PVC), while the portion of the tube in unit 32 comprises silicone rubber. Tube segments 26 and 28 and the portion of the tube in unit 32 may thus be regarded as a single tube. Alternatively, the tube segments and the portion of the tube in unit 32 may be fabricated as a unitary element from silicone or from another material with similar properties. The term "tube," in the context of the present patent application and in the claims, should thus be understood as referring both to unitary tubes and to any arrangement of tube segments and portions in series that defines a tube-like flow path.

As shown in detail in the figures that follow, mechanical interface unit 32 couples with pump 22 so as to bring the tube into engagement with the peristaltic mechanism of the pump. Typically, unit 32 is supplied as a pre-assembled, disposable kit, along with tube segments 26 and 28. Unit 32 is constructed so as to enable an operator 34 to connect the unit to pump 22 stably and reliably by fitting the unit against the pump and snapping it into place with only light pressure. Because the connection between unit 32 and pump 22 is self-aligning, operators are able to perform this operation with a single hand, after only minimal training. After use, unit 32 may be snapped off pump 22 and discarded together with the tube.

Figure 2:
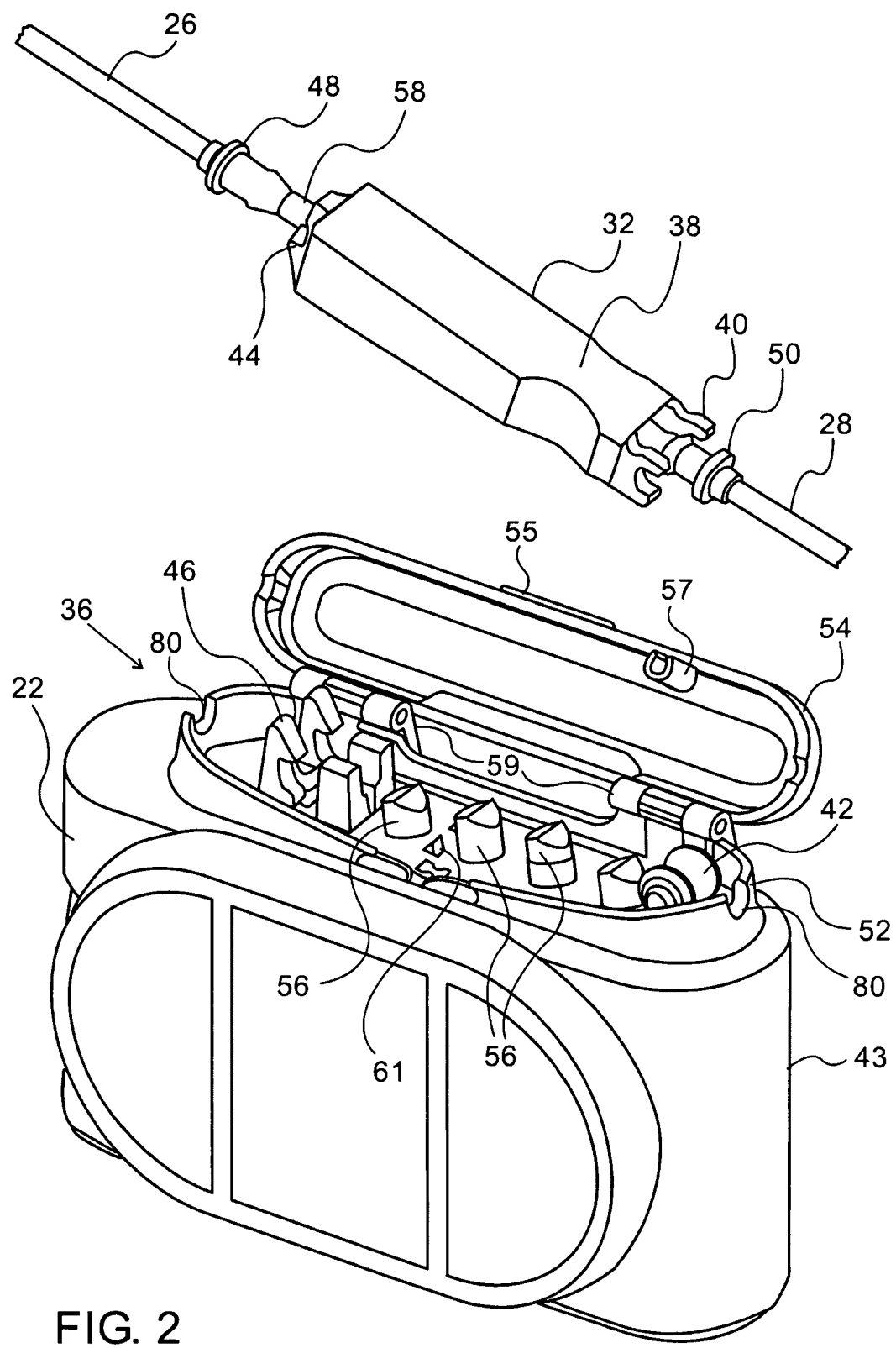
FIG. 2 is a schematic, pictorial illustration showing coupling of a mechanical interface unit with an infusion tube to an infusion pump, in accordance with an embodiment of the present invention.
Figure 3:
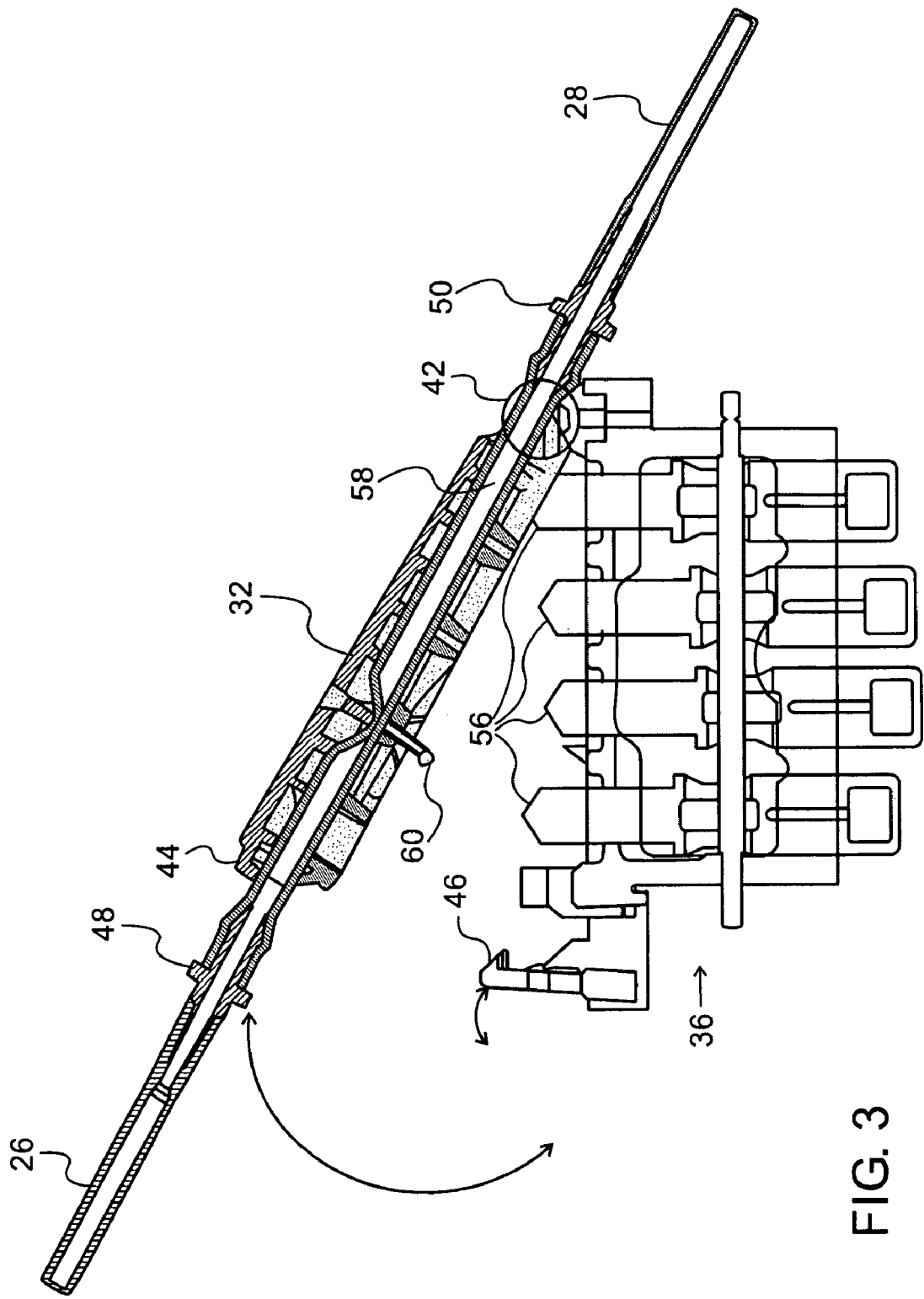
FIG. 3 is a schematic, sectional illustration of a part of an infusion pump and a mechanical interface unit during coupling of the mechanical interface unit to the infusion pump, in accordance with an embodiment of the present invention.

Reference is now made to FIGS. 2 and 3, which schematically show details of pump 22 and of mechanical interface unit 32 during preliminary stages of attaching the unit to the pump, in accordance with an embodiment of the present invention. FIG. 2 is a pictorial view, while FIG. 3 shows details of the mechanical interface unit and of a peristaltic mechanism 36 of the pump in sectional view.

Mechanical interface unit 32 comprises a body 38, which hold a portion 58 of the flexible infusion tube. In the embodiment shown in the figures, portion 58 of the tube is connected to segments 26 and 28 by connectors 48 and 50, respectively. Body 38 has an elongated shape, corresponding to the linear configuration of mechanism 36. Mechanism 36 comprises multiple fingers 56, which move up and down to compress and release tube portion 58 in a predetermined cyclic pattern, so as to propel fluid downstream from tube segment 26 to tube segment 28. Details of the operation of this sort of multi-finger peristaltic mechanism are described in the above-mentioned U.S. patent application Ser. No. 11/791,599 and in PCT Patent Applications PCT/IL2007/001398 and PCT/IL2007/001400, filed Nov. 13, 2007, whose disclosures are incorporated herein by reference.

Unit 32 comprises a hinge insert 40 at one end of body 38 (in this case, the downstream end) and a catch insert 44 at the other (upstream) end. To assemble unit 32 onto pump 22, the operator first brings hinge insert 40 into engagement with a hinge receptacle 42 on a body 43 of the pump. In this position, unit 32 is aligned in a plane of peristaltic mechanism 36 (i.e., the plane of the page in FIG. 3), but is able to rotate within the plane about an axis defined by the hinge receptacle. The operator rotates unit 32 about this axis, while the hinge insert engages the hinge receptacle, until catch insert 44 engages and locks onto a catch receptacle 46 on the pump body. The catch receptacle is spring-loaded (or otherwise elastic) so that it slides over and then locks onto the catch insert as the operator presses unit 32 down against pump 22. Once engaged and locked in this manner, movement of unit 32 is restricted in all directions. Unit 32 may subsequently be released from pump 22 simply by opening the catch and rotating the unit away from the pump.

The rotational mode of assembly described above is advantageous in that it ensures accurate alignment of tube portion 58 with mechanism 36, even in one-handed operation. Consequently, good flow accuracy is achieved without the need for very careful insertion of the tube into the pump. The inventors have found that the combination of this sort of mechanical interface unit with the type of peristaltic pump described in the above-mentioned patent applications gives better than 2.5% accuracy in flow control over long periods of time.

The position of hinge receptacle 42 may be pre-adjusted so that interface unit 32, when engaged and locked onto pump 22, is properly located relative to fingers 56. For example, the hinge receptacle may be connected to pump body 43 by a single screw (not shown), which permits the receptacle to be moved and then tightened in place in a factory calibration procedure. Because the hinge receptacle is located on the downstream side of mechanism 36, this sort of calibration can be used to find the optimal balance between pressure buildup and energy consumption for propelling fluid at high pressure.

Furthermore, this mode of assembly gives the operator a mechanical advantage in closing the catch insert against the catch receptacle, so that relatively little force is needed to make a secure connection. In a clinical version of system 20, the inventor has found that less than 2 kg of force, typically about 1.2 kg, is sufficient for this purpose.

Another advantage of mechanical interface unit 32 and the mating structure on pump 22 is that they ensure that the tube will be assembled onto the pump in the proper direction: Because one type of mating connector is used at the upstream end of unit 32, and a different type of mating connector is used at the downstream end, it is impossible for the operator to accidentally attach the tube in the reverse direction.

In the embodiment pictured in the figures, hinge receptacle 42 has the form of a split axle, while hinge insert 40 has the form of a split saddle. At the other end of unit 32, catch insert 44 has the form of a split tooth, while catch receptacle 46 comprises a dual, concave catch. Tube portion 58 thus passes through the opening between the sides of insert 40, receptacle 42, insert 44 and receptacle 46. This particular configuration of the hinge and catch parts of pump 22 and unit 32 has been found to provide mechanical stability, durability and ease of assembly.

On the other hand, other configurations of the hinge and catch parts are also possible, as will be apparent to those skilled in the art, and are considered to be within the scope of the present invention. For example, the "male" and "female" elements on the interface unit and pump body may be reversed, so that the hinge and catch inserts on the interface unit have the form of an axle and elastic catch, while the hinge and catch receptacles on the pump have the form of a saddle and tooth. Other suitable hinge and catch arrangements are described in the above-mentioned U.S. patent application Ser. No. 11/791,599.

After assembly of interface unit 32 onto pump 22, a cover 54 may be closed against a rim 52 over the unit for added security. A locking mechanism 55 on the cover prevents accidental opening. Pump 22 may comprise a sensor (not shown) for detecting whether cover 54 is closed, such as a magnetic sensor, which detects the proximity of a magnet 57 attached to the cover. Until the operator is ready to close the cover, however, spring-loaded hinges 59 hold the cover open so that it does not interfere with handling of the interface unit.

Interface unit 32 also comprises an anti-free-flow mechanism 60, which closes off tube portion 58 until the interface unit has been securely connected to pump 22, in order to prevent uncontrolled flow of infusion fluid into the patient's body. Mechanism 60 may be opened manually if necessary, and opens automatically when the interface unit is mounted on the pump. A key 61 on the pump body (FIG. 2) releases mechanism 60 if the mechanism was opened manually before mounting interface unit 32 on the pump, so as to ensure that the mechanism closes (and prevents inadvertent free flow) when the interface unit is disengaged from the pump. Details of this sort of anti-free-flow mechanism mechanism are described in the above-mentioned U.S. patent application Ser. No. 11/791,599 and in PCT Patent Application PCT/IL2007/001405, filed Nov. 13, 2007, whose disclosure is incorporated herein by reference.

Figure 4:
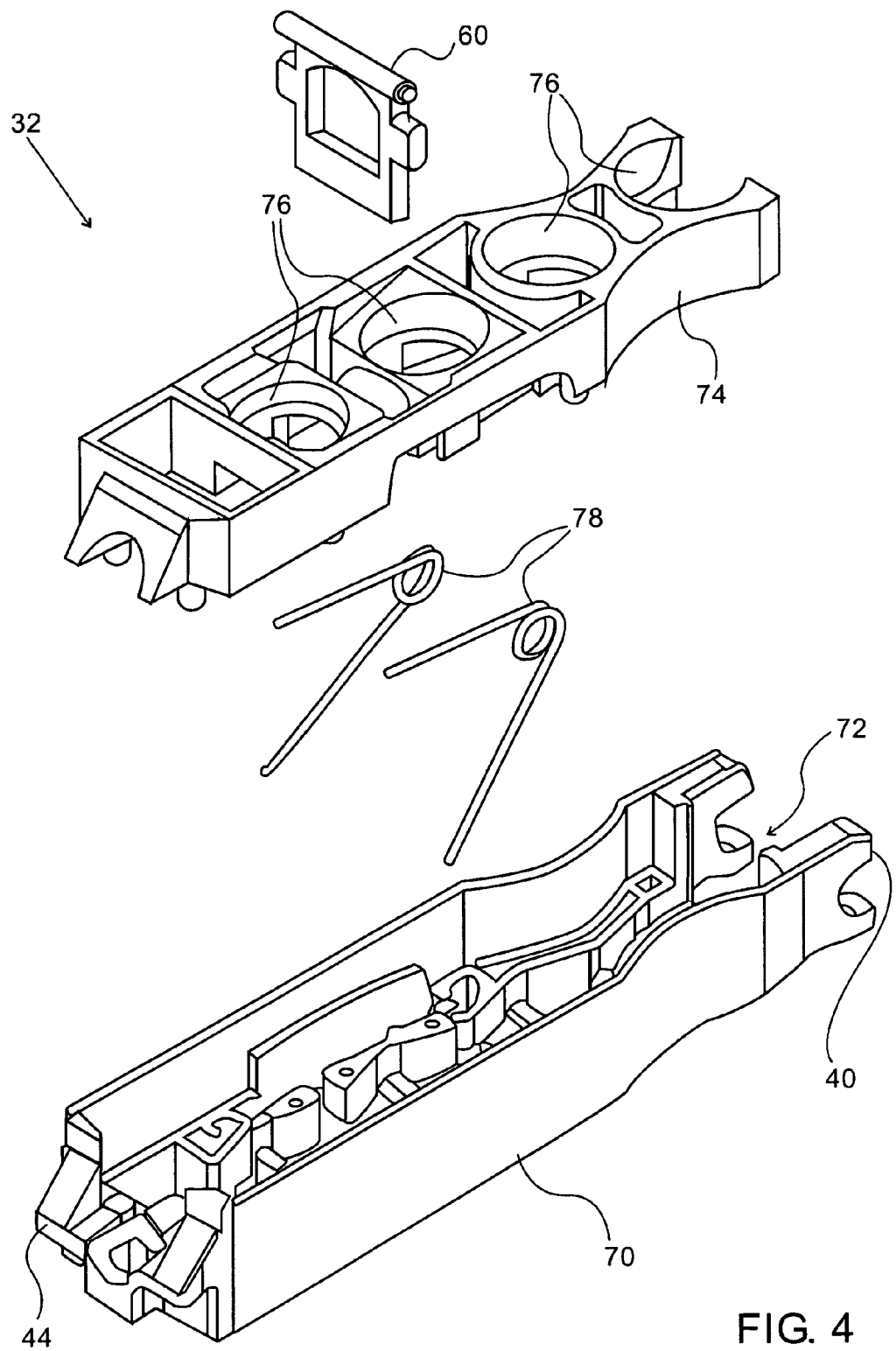
FIG. 4 is a schematic, exploded view of a mechanical interface unit, in accordance with an embodiment of the present invention.

FIG. 4 is a schematic, exploded view of interface unit 32, in accordance with an embodiment of the present invention. Unit 32 comprises an outer shell 70 and an inner shell 74, which define a central channel 72 for receiving tube portion 58. To assemble unit 32, tube portion 58 is placed in channel 72, and shells 70 and 74 are then fitted together, thus holding the tube portion securely in place. Anti-free-flow mechanism 60 is mounted in a slot in unit 32 against springs 78, which hold the mechanism in its closed position. (Alternatively, a single spring may be used for this purpose.) Shell 74 contains finger holes 76, through which fingers 56 protrude in order to engage and compress the tube portion inside.

Figure 5:
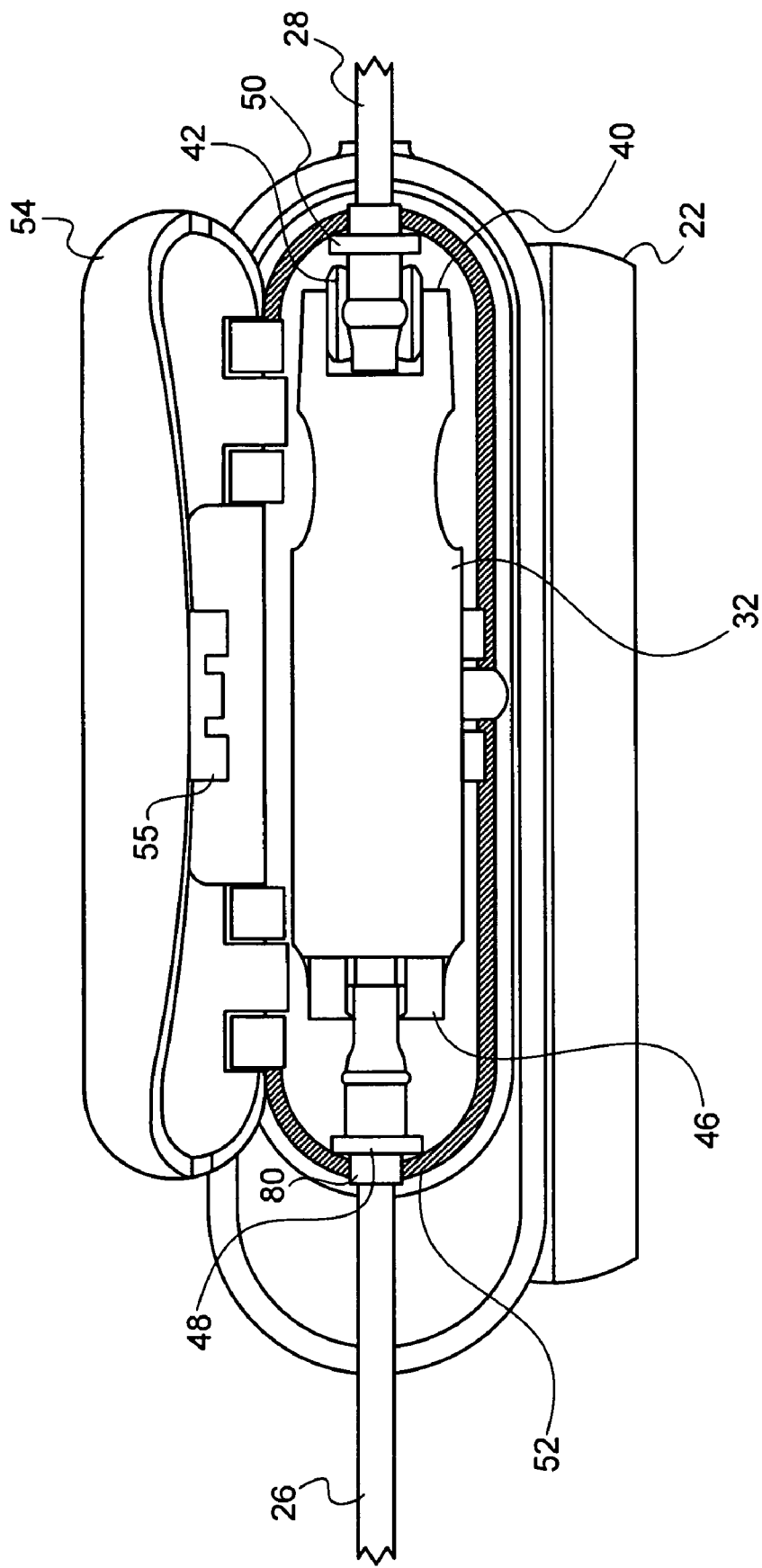
FIG. 5 is a schematic side view of an infusion pump to which a mechanical interface unit with an infusion tube has been coupled, in accordance with an embodiment of the present invention.
Figure 6:
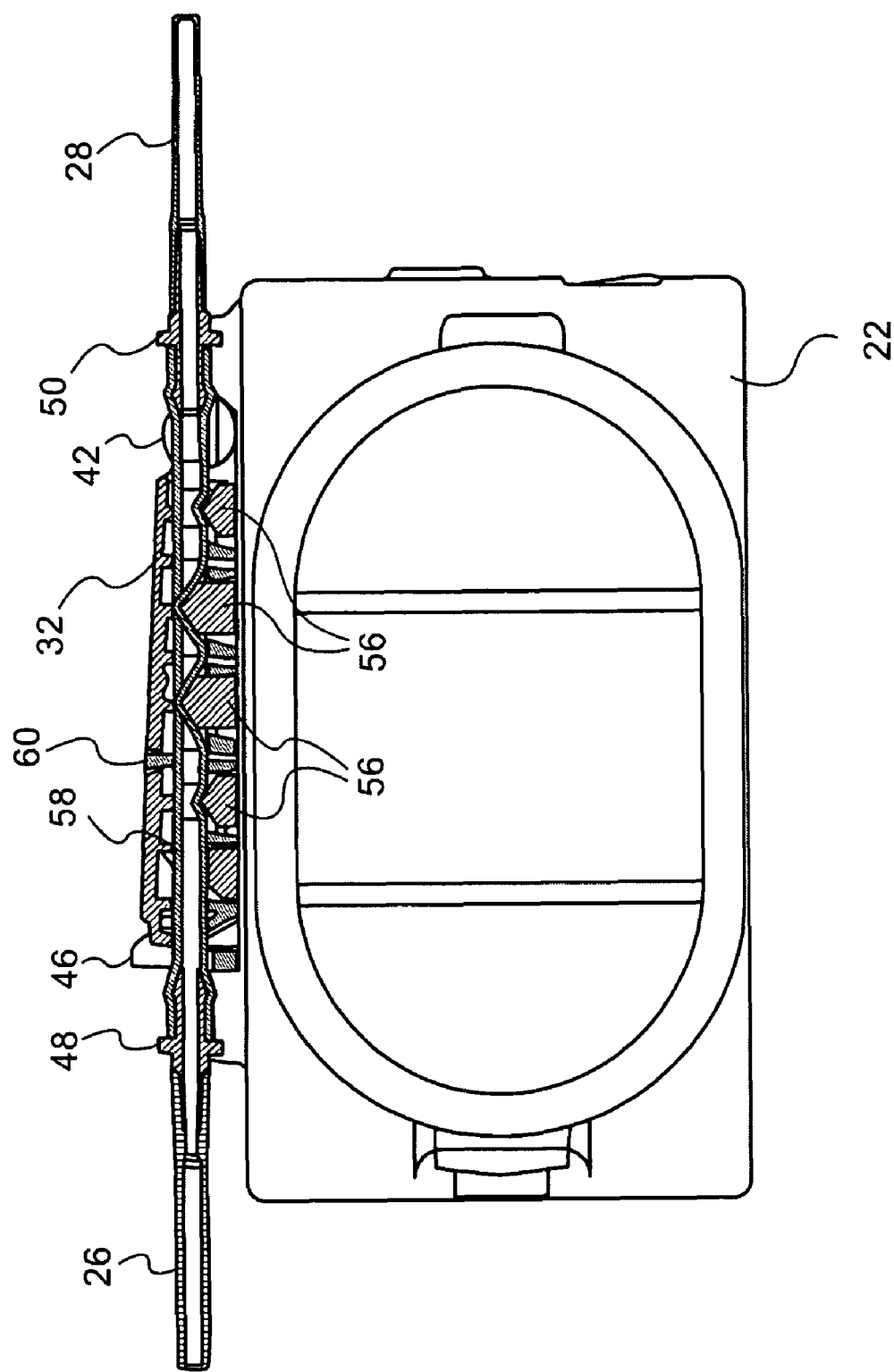
FIG. 6 is a schematic, frontal, partially sectional view of an infusion pump to which a mechanical interface unit with an infusion tube has been coupled, in accordance with an embodiment of the present invention.

Reference is now made to FIGS. 5 and 6, which show interface unit 32 assembled onto pump 22, in accordance with an embodiment of the present invention. FIG. 5 is a side view, while FIG. 6 is a frontal, partly sectional view. In these figures, catch receptacle 46 has closed over catch insert 44, thus bringing tube portion 58 into engagement with peristaltic mechanism 36 of pump 22. The peristaltic mechanism is thus able to propel the infusion fluid through the tube. Tube segments 26 and 28 protrude through holes 80 in rim 52, which are similar in shape and diameter to the tube segments. Collars on connectors 48 and 50, which have a larger diameter than the holes, lodge against the inner side of rim 52, thus enhancing the stability and security of unit 32, particularly against pulling forces that may be exerted on tubes 26 and 28. Anti-free-flow mechanism 60 is held open. Fingers 56 alternately compress and release tube portion 58 in the appropriate pattern, at a frequency chosen to give the desired volumetric flow of fluid through the tube.

Although the embodiment shown in the figures uses a particular type of linear finger-based mechanism, the principles of the present invention may similarly be applied to peristaltic pumps using other types of mechanisms, including cam-based mechanisms, as well as circular mechanisms. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus, comprising:
   an infusion pump, comprising:
      a pump body;
      a peristaltic mechanism, which protrudes from the pump body and is configured to exert a force on a flexible infusion tube so as to propel a fluid through the tube;
      a hinge receptacle which is fixed to the pump body and defines a hinge axis; and
      a catch receptacle fixed to the pump body; and
   a mechanical interface unit, which is configured to hold a portion of the tube, and which comprises:
      a hinge insert, which is configured to engage the hinge receptacle;
      a catch insert, which is configured to lock onto the catch receptacle upon rotation of the mechanical interface unit about the hinge axis while the hinge insert engages the hinge receptacle, so as to bring the tube into engagement with the peristaltic mechanism;
      a rim surrounding the peristaltic mechanism; and
      a door, which closes over the rim so as to enclose the peristaltic mechanism and to prevent unintentional detachment of the mechanical interface unit from the pump body.

2. The apparatus according to claim 1, wherein the peristaltic mechanism comprises multiple fingers, which are driven to compress and release the tube in a predetermined cyclic pattern.

3. The apparatus according to claim 1, wherein the peristaltic mechanism has a linear configuration, and wherein the mechanical interface has an elongated shape corresponding to the linear configuration of the peristaltic mechanism.

4. The apparatus according to claim 1, wherein the hinge receptacle comprises an axle, and the hinge insert comprises a saddle, which fits over the axle.

5. The apparatus according to claim 4, wherein the axle and saddle are split so as to define a channel for receiving the portion of the tube.

6. The apparatus according to claim 1, wherein the catch insert comprises a tooth, and the catch receptacle comprises an elastic catch.

7. The apparatus according to claim 1, wherein the mechanical interface unit comprises collars, which are fixed to opposing ends of the portion of the tube and lodge against the rim.

8. The apparatus according to claim 7, wherein the rim has openings shaped to receive the tube so that the tube extends through the openings when the door is closed.

9. The apparatus according to claim 8, wherein the collars are configured to lodge inside the rim and have respective diameters that are larger than the openings so as to prevent axial motion of the tube after the door has been closed.

10. The apparatus according to claim 1, wherein the mechanical interface unit comprises an anti-free-flow mechanism, which is configured to prevent flow of the fluid through the portion of the tube until the tube has been brought into the engagement with the peristaltic mechanism.

11. The apparatus according to claim 10, wherein the anti-free-flow mechanism can be latched opened into a latched open position prior to the engagement of the tube with the peristaltic mechanism, and wherein the infusion pump comprises a key, which is fixed to the pump body and is configured to release the anti-free-flow mechanism from the latched open position so as to prevent the flow of the fluid through the portion of the tube when mechanical interface unit is disengaged from the pump.

12. A medical device, comprising:
   an interface unit body, which is configured to hold a portion of a flexible infusion tube;
   a hinge insert, which is fixed to the interface unit body and is configured to engage a hinge receptacle, which defines a hinge axis, on an infusion pump;
   a catch insert, which is fixed to the interface unit body and is configured to lock onto a catch receptacle on the infusion pump upon rotation of the mechanical interface unit about the hinge axis while the hinge insert engages the hinge receptacle, so as to bring the tube into engagement with a peristaltic mechanism of the infusion pump in order to enable the peristaltic mechanism to propel a fluid through the tube;
   a rim surrounding the peristaltic mechanism; and
   a security door, which closes over the rim so as to enclose the peristaltic mechanism and to prevent unintentional detachment of the interface unit body from the peristaltic mechanism.

13. The device according to claim 12, wherein the peristaltic mechanism has a linear configuration, and wherein the interface unit body has an elongated shape corresponding to the linear configuration of the peristaltic mechanism.

14. The device according to claim 12, wherein the hinge receptacle comprises an axle, and the hinge insert comprises a saddle, which fits over the axle.

15. The device according to claim 14, wherein the axle and saddle are split so as to define a channel for receiving the portion of the tube.

16. The device according to claim 12, wherein the catch insert comprises a tooth, and the catch receptacle comprises an elastic catch.

17. The device according to claim 12, and comprising collars, which are fixed to opposing ends of the portion of the tube and are configured to lodge against a rim surrounding the peristaltic mechanism on the infusion pump.

18. The device according to claim 17, wherein the collars comprise connectors, which connect the portion of the flexible infusion tube in the housing to upstream and downstream tube segments.

19. The device according to claim 12, and comprising an anti-free-flow mechanism, which is configured to prevent flow of the fluid through the portion of the tube until the tube has been brought into the engagement with the peristaltic mechanism wherein the anti-free-flow mechanism can be latched open into a latched open position prior to the engagement of the tube with the peristaltic mechanism, and wherein the infusion pump comprises a key, which is fixed to the pump body and is configured to release the anti-free-flow mechanism from the latched open position so as to prevent the flow of the fluid through the portion of the tube when mechanical interface unit is disengaged from the pump.

20. A method for infusion, comprising:
   providing a mechanical interface unit, which holds a portion of a flexible infusion tube and comprises a hinge insert and a catch insert;
   opening a safety door to reveal a peristaltic mechanism;
   inserting the hinge insert into a hinge receptacle, which defines a hinge axis, on an infusion pump;
   rotating the mechanical interface unit about the hinge axis while the hinge insert engages the hinge receptacle, so as to bring the tube into engagement with a peristaltic mechanism of the infusion pump while the safety door is latched open;
   securing the safety door enclosing the peristaltic mechanism to prevent unintentional detachment of the mechanical interface unit from the peristaltic mechanism; and
   actuating the infusion pump while the tube is in engagement with the peristaltic mechanism so as to propel a fluid through the tube.

* * * * *